(12) United States Patent  (10) Patent No.: US 8,088,183 B2
Jackam et al.  (45) Date of Patent: Jan. 3, 2012

(54) PRODUCTION OF BIODIESEL AND GLYCERIN FROM HIGH FREE FATTY ACID FEEDSTOCKS

(75) Inventors: John P. Jackam, Butte, MT (US); Joel M. Pierce, Butte, MT (US); Jeffrey D. Jones, Butte, MT (US)

(73) Assignee: Seneca Landlord, LLC, Ames, IA (US)

( * ) Notice: Subject to any disclaimer, the term of this patent is extended or adjusted under 35 U.S.C. 154(b) by 284 days.

(21) Appl. No.: 11/504,828

(22) Filed: Aug. 15, 2006

(65) Prior Publication Data

US 2007/0277430 A1  Dec. 6, 2007

Related U.S. Application Data

(63) Continuation-in-part of application No. 10/766,740, filed on Jan. 26, 2004, now Pat. No. 7,806,945.

(60) Provisional application No. 60/537,251, filed on Jan. 15, 2004, provisional application No. 60/443,049, filed on Jan. 27, 2003.

(51) Int. Cl.
*C10L 1/18* (2006.01)
(52) U.S. Cl. ............................................ 44/308; 44/307
(58) Field of Classification Search ................... 554/167; 549/413; 44/308, 307
See application file for complete search history.

(56) References Cited

U.S. PATENT DOCUMENTS

| | | | |
|---|---|---|---|
| 1,659,790 A | 2/1928 | Starrels | |
| 2,290,609 A | 7/1942 | Goss et al. | |
| 2,383,580 A | 8/1945 | Clarence et al. | |
| 2,383,581 A | 8/1945 | Clarence et al. | |
| 2,383,601 A | 8/1945 | Kelm | |
| 2,385,599 A | 8/1945 | Glossop | |
| 2,383,596 A | 8/1948 | Dreger | |

(Continued)

FOREIGN PATENT DOCUMENTS

DE  197 24 018 A  12/1998

(Continued)

OTHER PUBLICATIONS

Noureddini et al., Glycerolysis of Fats and Methyl Esters, JAOCS, 1997, pp. 419-425, vol. 74, No. 4, AOCS Press, Lincoln, Nebraska.

(Continued)

*Primary Examiner* — Michael Marcheschi
*Assistant Examiner* — Chantel Graham
(74) *Attorney, Agent, or Firm* — Ryan N. Carter; Glenn Johnson (57) ABSTRACT

A system and method for the conversion of free fatty acids to glycerides and the subsequent conversion of glycerides to glycerin and biodiesel includes the transesterification of a glyceride stream with an alcohol. The fatty acid alkyl esters are separated from the glycerin to produce a first liquid phase containing a fatty acid alkyl ester rich (concentrated) stream and a second liquid phase containing a glycerin rich (concentrated) stream. The fatty acid alkyl ester rich stream is then subjected to distillation, preferably reactive distillation, wherein the stream undergoes both physical separation and chemical reaction. The fatty acid alkyl ester rich stream is then purified to produce a purified biodiesel product and a glyceride rich residue stream. The glycerin rich second liquid phase stream may further be purified to produce a purified glycerin product and a (second) wet alcohol stream.

19 Claims, 6 Drawing Sheets

U.S. PATENT DOCUMENTS

| | | |
|---|---|---|
| 2,494,366 A | 1/1950 | Sprules et al. |
| 2,543,421 A | 2/1951 | Price et al. |
| 2,588,435 A | 3/1952 | Van et al. |
| 2,808,421 A | 10/1957 | Brokaw |
| 2,875,221 A | 2/1959 | Birnbaum |
| 3,102,129 A | 8/1963 | Birnbaum et al. |
| 3,459,736 A | 8/1969 | Dalibor |
| 4,164,506 A | 8/1979 | Kawahara et al. |
| 4,267,393 A | 5/1981 | Torck et al. |
| 4,303,590 A | 12/1981 | Tanaka et al. |
| 4,364,743 A | 12/1982 | Erner |
| 4,371,470 A | 2/1983 | Matsukura et al. |
| 4,668,439 A * | 5/1987 | Billenstein et al. ........... 554/167 |
| 4,695,411 A | 9/1987 | Stern et al. |
| 4,698,186 A | 10/1987 | Jeromin et al. |
| 4,839,287 A | 6/1989 | Holmberg et al. |
| 4,956,286 A | 9/1990 | Macrae |
| 5,354,878 A | 10/1994 | Connemann et al. |
| 5,399,731 A | 3/1995 | Wimmer |
| 5,424,467 A | 6/1995 | Bam et al. |
| 5,434,279 A | 7/1995 | Wimmer |
| 5,514,820 A | 5/1996 | Assmann et al. |
| 5,525,126 A | 6/1996 | Basu et al. |
| 5,578,090 A | 11/1996 | Bradin |
| 5,646,311 A * | 7/1997 | Hunt et al. .................... 549/413 |
| 5,697,986 A | 12/1997 | Haas |
| 5,713,965 A | 2/1998 | Foglia et al. |
| 5,847,239 A | 12/1998 | Davey et al. |
| 5,908,946 A | 6/1999 | Stern et al. |
| 6,013,817 A | 1/2000 | Stern et al. |
| 6,015,440 A | 1/2000 | Noureddini |
| 6,075,158 A | 6/2000 | Hill |
| 6,090,959 A | 7/2000 | Hirano et al. |
| 6,127,560 A * | 10/2000 | Stidham et al. ............... 554/167 |
| 6,127,561 A | 10/2000 | Jeromin et al. |
| 6,174,501 B1 | 1/2001 | Noureddini |
| 6,211,390 B1 | 4/2001 | Peter et al. |
| 6,262,285 B1 | 7/2001 | McDonald |
| 6,288,251 B1 | 9/2001 | Tsuto et al. |
| 6,398,707 B1 | 6/2002 | Wu et al. |
| 6,399,800 B1 | 6/2002 | Haas et al. |
| 6,440,057 B1 | 8/2002 | Ergun et al. |
| 6,489,496 B2 | 12/2002 | Barnhorst et al. |
| 6,500,974 B2 | 12/2002 | Thengumpillil et al. |
| 6,642,399 B2 | 11/2003 | Boocock |
| 6,822,105 B1 | 11/2004 | Luxem et al. |
| 6,965,043 B1 | 11/2005 | Kenneally et al. |
| 7,087,771 B2 | 8/2006 | Luxem et al. |
| 7,528,272 B2 | 5/2009 | Alasti |
| 2002/0111504 A1 | 8/2002 | Peter et al. |
| 2002/0156305 A1 | 10/2002 | Turck |
| 2003/0083514 A1 | 5/2003 | Boocock |
| 2003/0149289 A1 | 8/2003 | Suppes |
| 2003/0229238 A1 | 12/2003 | Fleisher |

FOREIGN PATENT DOCUMENTS

| | | |
|---|---|---|
| EP | 0591019 B1 | 8/1997 |
| EP | 0708813 B2 | 2/2001 |
| GB | 587532 | 4/1947 |
| GB | 612667 | 11/1948 |
| GB | 2 350 618 A | 12/2000 |
| WO | WO 95/02661 | 1/1995 |
| WO | 9924387 | 5/1999 |
| WO | WO02/28811 A1 | 4/2002 |
| WO | WO02/38529 A1 | 5/2002 |

OTHER PUBLICATIONS

Tyson, Brown Grease Feedstocks for Biodiesel, WWW domain nrel.gov, 2002, pp. 1-33, National Renewable Energy Laboratory, Boulder, CO.

Tyson, Biodiesel Technology and Feedstocks, WWW domain nrel.gov, 2003, pp. 1-37, National Renewable Energy Laboratory, Boulder, CO.

Clements, Pretreatment of High Free Fatty Acid Feedstocks, Biodiesel Production Technology Workshop III, Mar. 26-28, 2003, pp. 78c-78i, Iowa State University, Lincoln, Nebraska.

Muniyappa et al; Improved Conversion of Plant Oils and Animal Fats Into Biodiesel and Co-Product; Jun. 1996; Elsevier Science Limited, 0960-8524/96.

Tyson, Biodiesel Research Progress 1992-1997; pp. 1-301; National Renewable Energy Laboratory; Boulder Co.; Feb. 1997.

Gerpen et al; Biodiesel Production Technology Aug. 2002-Jan. 2004; pp. 1-106; Jul. 2004; National Renewable Energy Laboratory; Boulder Co.

Biodiesel in North America: Implementation Issues; IEA Bioenergy Task 39; pp. 1-165; Feb. 28, 2004; S&T Consultants Inc., Canada.

Hildebrandt; Kinetic Investigation of the Base-Catalyzed Glycerolysis of Fatty Acid Methyl Esters; pp. 1-183; Nov. 5, 2004.

Lago, R. C. A., R. R. Szpiz, F. H. Jablonka, D. A. Pereira and L. Hartman; "Extraction and Transesterification of Vegetable Oils with Ethanol"; 1985, pp. 147-154; vol. 40, No. 3, Oleagineux; Paris, France.

Ma, Fangrui and Milford A. Hannah; "Biodiesel Production: a review"; 1999, pp. 1-15; vol. 70, No. 1, Bioresource Technology Elsevier, GB.

Kiss, A.A., A.C. Dimian, F. Omota, "Sustainable biodiesel production by integrated process design", 2005, van't Hoff Institute for Molecular Sciences, University of Amsterdam, The Netherlands.

Yuan, W. et al. Vapor pressure and normal boiling point predictions for pure methyl esters and biodiesel fuels, Fuel, 84, 2005, 943-950.

Gouw, T.H. et al. The Journal of the American Oil Chemists' Society, 1964, 41, 142-145.

\* cited by examiner

PRODUCTION OF BIODIESEL AND GLYCERIN FROM HIGH FREE FATTY ACID FEEDSTOCKS

This application is a continuation-in-part application of U.S. application Ser. No. 10/766,740, filed on Jan. 26, 2004, now U.S. Pat. No. 7,806,945, which claims the benefit of U.S. Patent Application Ser. Nos. 60/443,049, filed Jan. 27, 2003, and 60/537,251, filed Jan. 15, 2004, each of which is hereby incorporated.

FIELD OF THE INVENTION

The present invention relates to improved processes and systems for biodiesel production.

BACKGROUND OF THE INVENTION

There is continued and growing interest in the use of renewable resources as replacements for petroleum-derived chemicals. Fatty acid alkyl esters (FAAEs) produced from fats and oils have been investigated as replacements for such petroleum-derived materials, particularly diesel fuel.

It has long been known that triglycerides from fats and oils can be used as fuels for diesel engines. However, such use typically results in engine failure. Remedies for such engine failure wherein conversion of fatty acids, found in lipids, into simple esters, such as methyl and ethyl esters, has been proposed. See, for instance, the process described in U.S. Pat. No. 6,398,707. An increasing body of evidence indicates that these esters perform well in essentially unmodified diesel engines and that such esters may effectively reduce the output of particulate and hydrocarbon pollutants relative to petroleum-diesel fuel. The term "biodiesel" is applied to these esters.

Processes for biodiesel production have been known for many years. For instance U.S. Pat. No. 4,164,506 discloses a biodiesel synthesis wherein fatty acids are subjected to acid catalysis. The conversion of triglycerides with base catalysis is described in U.S. Pat. Nos. 2,383,601 and 2,494,366. Conversion of both free fatty acids and triglycerides with enzyme catalysis is disclosed in U.S. Pat. Nos. 4,956,286, 5,697,986 and 5,713,965. None of these processes, however, completely addresses the production of biodiesel from low value high free fatty acid feedstocks.

An economic analysis of any process for the production of biodiesel indicates that feedstock cost is the largest portion of production cost for biodiesel. Whereas a 15 weight percent free fatty acid (FFA) feedstock is the highest content that any contemporary commercial process has proposed to handle, producers (in order to conserve costs) would prefer to use feedstocks having up to 100 weight percent FFA content.

Further, most of the processes of the prior art are unattractive because they rely upon acid catalyzed esterification of fatty acids. Acid catalysis is not suitable for processing such feedstocks containing FFA concentrations for two principal reasons. First, an excessive amount of acid catalyst is required in order to fully convert feedstocks having high FFA content. Since the acid catalyst must be neutralized before processing the glycerides, the increased catalyst loading results in an excessive amount of generated salt. Further, such processes generate a large volume of waste water as disclosed in U.S. Pat. Nos. 4,303,590, 5,399,731 and 6,399,800.

While enzymatic catalysis has been reported in the literature for esterification of free fatty acids, it is disadvantageous because of reaction product inhibition from the presence of water which results when the free fatty acids in the feedstock are esterified with enzymes. Another problem evidenced from enzymatic processing is the high cost of enzymatic catalysts. Further, enzymatic catalysts have a limited life.

To avoid two-phase operation in packed bed and other reaction settings, some conventional processes for biodiesel production use volatile, toxic co-solvents. Such a process is disclosed in U.S. Pat. No. 6,642,399 B2. The use of volatile, toxic co-solvents is environmentally unacceptable.

Further, some prior art processes for producing biodiesel employ water to wash residual glycerin and salts from the FAAEs. This, however, generates a large volume of wastewater and increases the risk of forming FAAE emulsions, as disclosed in U.S. Pat. No. 5,399,731.

To be economically profitable, the biodiesel industry must take advantage of lower cost feedstocks. Yield is a very important criterion as feedstock costs approach two thirds of the total cost of production of biodiesel. To gain market share in the fuels industry, biodiesel must be competitively priced with conventional hydrocarbon diesel.

Alternative processes need to be developed which do not require high pressures or acid catalysis. In addition, such processes should not employ toxic co-solvents or water for the extraction of impurities. Such processes also need to produce high yield of biodiesel as well as employ inexpensive feedstocks. Further, such feedstocks need to have a high FFA content in order to be competitive with petrodiesel.

SUMMARY OF THE INVENTION

A process is disclosed which combines several unit operations into an economical and unique process for the conversion of free fatty acids to glycerides and the subsequent conversion of glycerides to glycerin and FAAEs. The fatty acid alkyl esters of the invention produced in accordance with the invention are typically fatty acid methyl esters though other fatty acid alkyl esters may be produced.

The invention relates to a process for converting low-value, high free fatty acid (FFA) feedstocks to biodiesel and high quality glycerin at a market price comparable to that of petroleum derived diesel fuels. The process of the invention therefore substantially departs from conventional concepts and designs of the background art. In so doing, the inventive process provides a process and apparatus primarily developed for the purpose of producing fatty acid alkyl esters and high quality glycerin from any low-value high free fatty acid feedstock.

Another aspect of the invention relates to separation and purification of major by-products of biodiesel production to render glycerin at a purity level greater than 95 or 99.7 percent, with non-detectable levels of alcohol and less than 0.5 percent weight/weight (w/w) salts.

The invention further relates to minimization of waste streams during normal operations, the use of lower operating temperatures and pressures than other commercial biodiesel processes, the non-use of toxic co-solvents and the production of a high quality glycerin byproduct.

In a preferred embodiment, the process is a continuous process.

The major steps of the process include the transesterification of a glyceride stream with an alcohol, preferably in the presence of base catalyst, to convert the glycerides to fatty acid alkyl esters and glycerin.

The fatty acid alkyl esters are then separated from the glycerin to produce a first liquid phase containing a fatty acid alkyl ester rich stream and a second liquid phase containing a glycerin rich stream.

The fatty acid alkyl ester rich stream is then subjected to distillation, preferably reactive distillation, wherein the stream undergoes both separation and chemical reaction. By means of reactive distillation, the stream is separated into a bottoms fraction containing a plurality of the fatty acid alkyl esters and an overhead fraction (principally of alcohol, a first wet alcohol stream), while simultaneously chemically reacting two or more stream components together in such a way as to remove unwanted impurities in one or more output stream(s). Such reactive distillation for example increases the yield amount of glycerides exiting the distillation column while increasing the purity of the biodiesel exiting the distillation column. The combination of chemical reaction and separation offers distinct advantages over conventional processes.

The fatty acid alkyl ester rich stream is then purified to produce a biodiesel product and a glyceride rich residue stream.

The glycerin rich second liquid phase stream may further be purified to produce a purified glycerin product and a (second) wet alcohol stream. A portion of the purified glycerin product may then be recycled into a glycerolysis reactor (in a glycerolysis process described in more detail below) for reaction with the free fatty acids.

The wet alcohol streams may further be purified, preferably continuously, to produce a purified alcohol product. Further, at least a portion of the purified alcohol product may be recycled into the transesterification reactor for reaction with the glycerides.

Neutralization of the alkaline stream, formed during the alkali-catalyzed transesterification process, may proceed by the addition of a mineral acid or more preferably an organic acid to the stream. Neutralization may occur by addition of the acid to the transesterification effluent stream directly or to the fatty acid alkyl ester rich stream and/or glycerin rich stream after such streams have been separated from the transesterification effluent stream.

BRIEF DESCRIPTION OF THE DRAWINGS

The features of the invention will be better understood by reference to the accompanying drawings which illustrate presently preferred embodiments of the invention. In the drawings.

DETAILED DESCRIPTION OF THE PREFERRED EMBODIMENTS

In the process of the invention, biodiesel is prepared by reacting glycerides with an alcohol in a transesterification reactor to produce fatty acid alkyl esters. This reaction typically occurs in the presence of an alkali catalyst. The alcohol is typically a $C_1$-$C_5$ alcohol, preferably methanol.

The resulting transesterification effluent stream may then be separated into a fatty acid alkyl ester rich stream and a glycerin rich stream. Each of these streams may then be purified to maximize the efficiency in recovery of biodiesel, glycerin and alcohol.

The alkaline transesterification effluent stream formed during the alkali-catalyzed transesterification process may be directly treated with a neutralizing agent, such as a mineral acid or an organic acid. Alternatively, the neutralizing agent may be added to the fatty acid alkyl ester rich stream and/or the glycerin rich stream after the streams have been separated from the transesterification effluent stream. Fatty acid alkyl esters are recovered from this pH adjusted stream.

Subsequent to neutralization, the neutralized stream may further be purified, such as by distillation or fractionation.

The process of the invention may further consist of an esterification step wherein a free fatty acid feedstock is first converted to glycerides. The resulting glycerides are then introduced into the transesterification reactor.

The use of the acid as neutralizing agent converts soaps, formed in the transesterification reactor, to free fatty acids. The soap forms from the action of caustic with fatty acids in the transesterification reactor. The presence of the soap makes it very difficult to effectuate phase separation between the fatty acid alkyl esters and the solution of glycerin, water, alcohol and salt. As a result, the soap emulsifies and retains much of the fatty acid alkyl esters in the glycerin rich phase. Purification of the glycerin rich phase is therefore complicated by the presence of the soap and the yield of alkyl esters is decreased.

Figure 3:
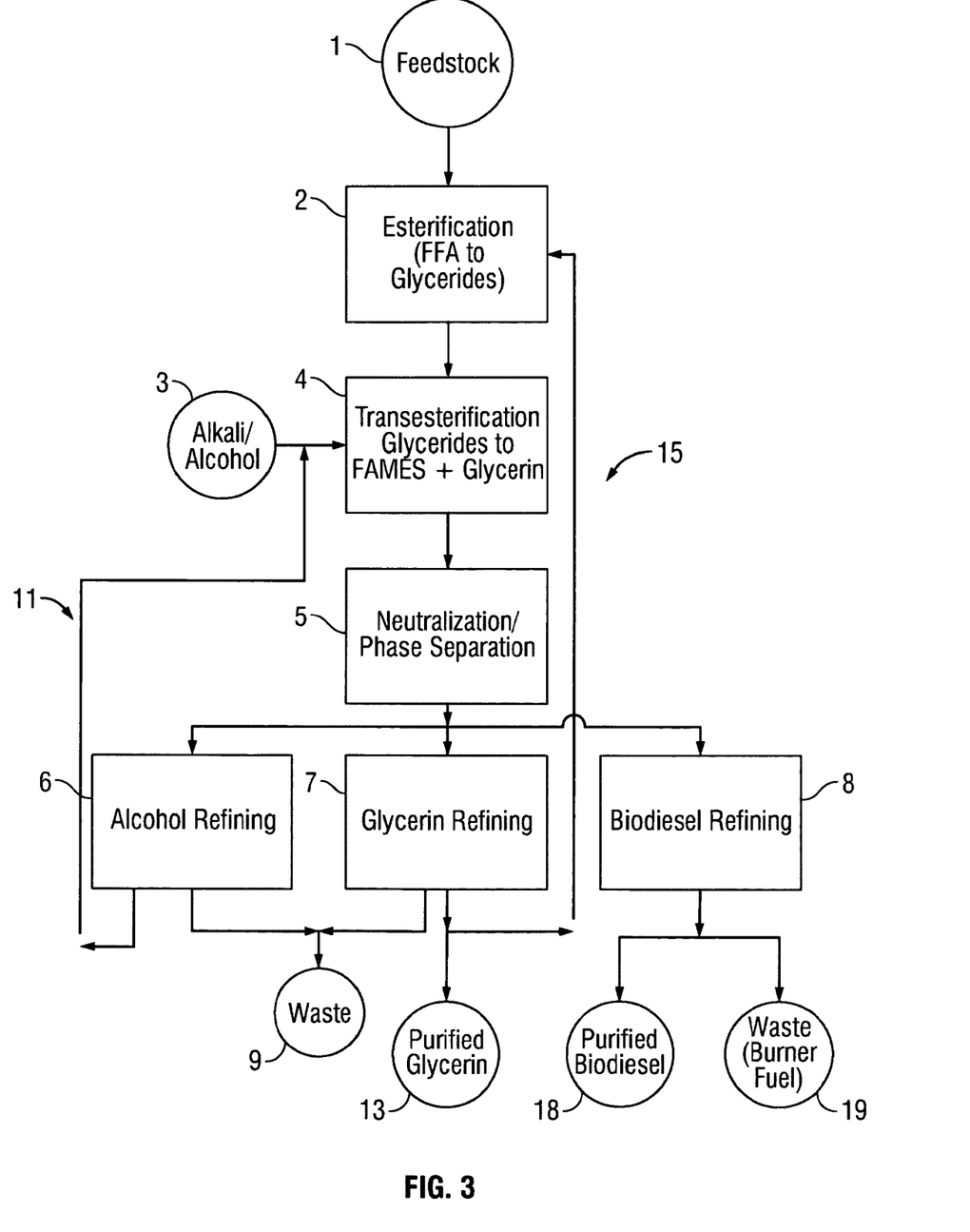
FIG. 3 is a schematic block diagram showing the basic steps of the production of biodiesel in accordance with the process of the invention.

An overview of the process of the invention may be presented in FIG. 3 wherein a feedstock 1 containing free fatty acids is introduced into a glycerolysis reactor 2 with glycerin wherein the free fatty acids are converted to glycerides. The glycerides are then introduced into transesterification reactor 4 with alcohol wherein the glycerides are transesterified to form fatty acid alkyl esters and glycerin. The alcohol/alkali stream 3 may be introduced into transesterification reactor 4 as a combined mixture of alkali catalyst and alcohol, or alternatively the alkali catalyst and alcohol may be introduced into the transesterification reactor as separate streams into transesterification reactor 4. The transesterification effluent stream or a portion thereof is then neutralized during neutralization/phase separation step 5, either before or after the effluent stream is separated into a fatty acid alkyl ester rich stream and a glycerin rich stream. Ultimately, alcohol, glycerin and biodiesel may be refined in alcohol refining step 6, glycerin refining step 7 and biodiesel refining step 8, respectively. The alcohol typically exits the system as a small portion of waste stream 9 or is recycled via flow 11 back to the transesterification reactor. Refined glycerin is isolated in technical grade glycerin stream 13 or may be recycled back via flow 15 to the glycerolysis reactor. The alkyl esters may further be refined in biodiesel refining step 8 to produce purified biodiesel stream 18 or may exit the system as a portion of waste stream 19 which may be useful, for example, as a burner fuel.

The process of the invention may be a continuous process wherein one or more of the following steps are carried out in a continuous fashion:

(1) the optional conditioning of a fatty acid containing feedstock by heating, mixing and filtering;

(2) continuously reacting the free fatty acids in the feedstock with glycerin in a glycerolysis reactor to produce glycerides;

(3) reacting the glycerides in a transesterification reactor with alcohol to render fatty acid alkyl esters and glycerin. This reaction preferably occurs in the presence of an alkali catalyst;

(4) separating fatty acid alkyl esters and glycerin from the transesterification effluent stream to yield a fatty acid alkyl ester rich stream and a glycerin rich stream, optionally separating the fatty acid alkyl ester and glycerin from the transesterification effluent stream by reactive distillation wherein a reaction in the distillation or fractionation column assists in the separation of the fatty acid alkyl esters and glycerin;

(5) purifying the fatty acid alkyl ester rich stream and recovering alcohol from the stream. The resultant purified fatty acid alkyl ester is acceptable for use as biodiesel;

(6) purifying the glycerin rich stream, preferably by use of an organic acid, such as a weak organic acid like acetic acid, formic acid or propionic acid, and recovering alcohol from the stream. The purified glycerin may then be introduced into the glycerolysis reactor;

(7) purifying the wet alcohol streams resulting from steps (5) and (6) above and removing water from the streams; and (8) recycling at least a portion of the purified alcohol to the transesterification reactor for reaction with the glyceride.

The feedstock, from which the biodiesel may be produced, typically contains a plurality of free fatty acids. The feedstock typically contains between from about 3 to about 100 weight percent of free fatty acids and, optionally, a fat and/or an oil.

Typically, the feedstock is a lipid feedstock. The free fatty acid feedstock for use in the invention may be a low-grade lipid material derived from animal fats and vegetable oils, including recycled fats and oils. For instance, the feedstock for the production of biodiesel fuel may be a grease feedstock, such as a waste grease or a yellow grease. Such low-grade lipid materials are very complex and typically are difficult to economically process using current state of the art processes because of their high free fatty acid levels (ranging from a few percent to 50 percent, and higher). In addition, such materials contain unprocessable material and contaminants that must be removed prior to processing or during refinement of the products.

The feedstock may be first introduced into a conditioning vessel or reactor that is operative to heat, mix and/or filter the feedstock to produce a conditioned feedstock. The feedstock may then be filtered, such as by using a traveling screen.

Subsequent to filtration, the concentration of free fatty acids in the conditioned lipid feedstock may be measured. Optionally, the concentration of free fatty acids in the conditioned feedstock may be continuously measured throughout the process. Measurements may be made with an in-line free fatty acid titration device that is operative to quantify the concentration of the free fatty acid in the conditioned feedstock.

During conditioning, the feedstock may be heated to a temperature in the range of about 35° C. to about 65° C., preferably between from about 55° C. to about 65° C., while mixed. A uniform mixture of glycerides, free fatty acids and unsaponifiable materials are typically present in the conditioned feedstock.

During glycerolysis, glycerin is used as a reactant to convert the free fatty acids in the feedstock to glycerides (mono-, di-, and triglyceride). Reaction of the free fatty acids in the feedstock typically occurs in the absence of a catalyst. In the glycerolysis reactor, the free fatty acid in the feedstock is mixed and continuously reacted with glycerin at an appropriate temperature and pressure to render a glycerolysis reactor effluent stream that contains generally less than about 0.5 percent by weight of free fatty acids and a plurality of glycerides. Glycerolysis typically occurs in the absence of both catalyst and co-solvent.

The glycerin, typically a purified glycerin product, is normally added to the glycerolysis reactor at a rate that is greater than the stoichiometric amount of glycerin required for the glycerolysis reaction. The amount of glycerin introduced to the glycerolysis reactor is generally in a stoichiometric proportion of about 3:1 of free fatty acid to glycerin in order to render the glyceride. In a preferred embodiment, the amount of glycerin added to the glycerolysis reactor is at a rate in the range of about 35 percent to about 400 percent of the stoichiometric amount of free fatty acids in the feedstock.

Preferably, glycerolysis is conducted at a temperature in the range of about 150° C. to about 250° C., typically from about 180° C. to about 250° C., more typically from about 180° C. to 230° C. The reaction typically proceeds under agitation. The reaction is further typically conducted at a pressure of about 0.1 pounds per square inch absolute to about 7 pounds per square inch absolute.

Reaction of the free fatty acids and glycerin typically occurs in the absence of a catalyst. The glycerolysis reactor effluent stream may contain less than 0.5 percent by weight of free fatty acids and a plurality of glycerides.

The glycerolysis is typically a continuous reaction. The continuous reaction of the free fatty acid in the feedstock with glycerin to produce the glyceride in the glycerolysis reactor may be conducted in response to a signal from the in-line fatty acid titration device.

During glycerolysis, water is removed; the produced glycerides being essentially water-free. Water is typically continuously removed from the glycerolysis reactor as a vapor through a fractionation column or a vent in the reactor headspace. Preferably, the vapor vented from the glycerolysis reactor is fractionated to yield a liquid fraction having a high concentration of glycerin and a vapor fraction or second liquid fraction having a high concentration of water. The liquid fraction containing the glycerin may then be returned to the glycerolysis reactor.

The glycerolysis reactor may consist of two or more continuous stirred tank reactors operated in series. The residence time of such reactors is typically not more than about 500 minutes, and preferably not more than 200 minutes.

A plurality of glycerides contained in the glycerolysis effluent stream are reacted with an alcohol in the transesterification reactor, such as a continuous stirred tank reactor. In this reaction, the glycerides in the glycerolysis reactor effluent stream are transesterified into fatty acid alkyl esters and glycerin. Transesterification proceeds at an appropriate temperature and pressure to produce the desired transesterification reactor effluent stream.

Transesterification, which preferably is a continuous process, occurs in the presence of a base catalyst. Suitable base catalysts include such alkali catalysts as potassium hydroxide and sodium hydroxide. The alkali catalyst may be added to the transesterification reactor at a rate sufficient to catalyze the reaction. Typically, the amount of alcohol added to the transesterification reactor is from about 0.5 percent by weight to 2.0 percent by weight of the glycerides present in the glycerolysis effluent stream.

Alternatively, an alkoxide, such as potassium methylate, may be added to the transesterification reactor to facilitate the base catalysis. As such, the rapid conversion of glycerides to alkyl esters may occur in the presence of caustic alkoxide, such as caustic methoxide catalysts.

The transesterification reaction typically occurs at a temperature in the range of about 25° C. to about 65° C., preferably from about 55° C. to about 65° C., and at a pressure of about 14.5 psia to about 3,625 psia.

The alcohol is normally added to the transesterification reactor at a rate that is greater than the stoichiometric amount of alcohol required for the alkali catalyzed transesterification reaction. For instance, the alcohol may be added to the transesterification reactor at a rate equal to about 200 percent of the stoichiometric amount of alcohol required for the catalyzed reaction.

Preferably, multiple alcohol or catalyst additions are made to the transesterification reactor.

The transesterification reactor typically contains at least two continuous stirred tank reactors that are operated in series. Each of the tank reactors typically has a residence time of about 15 to about 90 minutes, typically about 60 minutes.

The resulting transesterification reactor effluent stream contains a fatty acid alkyl ester and glycerin. Preferably, at least a portion of the glycerin is removed from the transesterification reactor before the plurality of glycerides are reacted with the alcohol.

A plurality of the resulting fatty acid alkyl esters may then be separated from the glycerin in the transesterification effluent stream. Separation into two distinct immiscible phases, i.e., a first liquid phase in which the plurality of fatty acid alkyl esters may be concentrated and a second liquid phase in which glycerin may be concentrated, is typically dependent upon the differences in densities in the two phases and employs gravitational force and/or centrifugal force.

Typically, the two phases are separated at a temperature of about 25° C. to about 65° C. to produce the fatty acid alkyl ester rich stream and glycerin rich stream. This separation process may be a continuous operation and may be performed in a clarifier or by means of membrane filtration.

Figure 6:
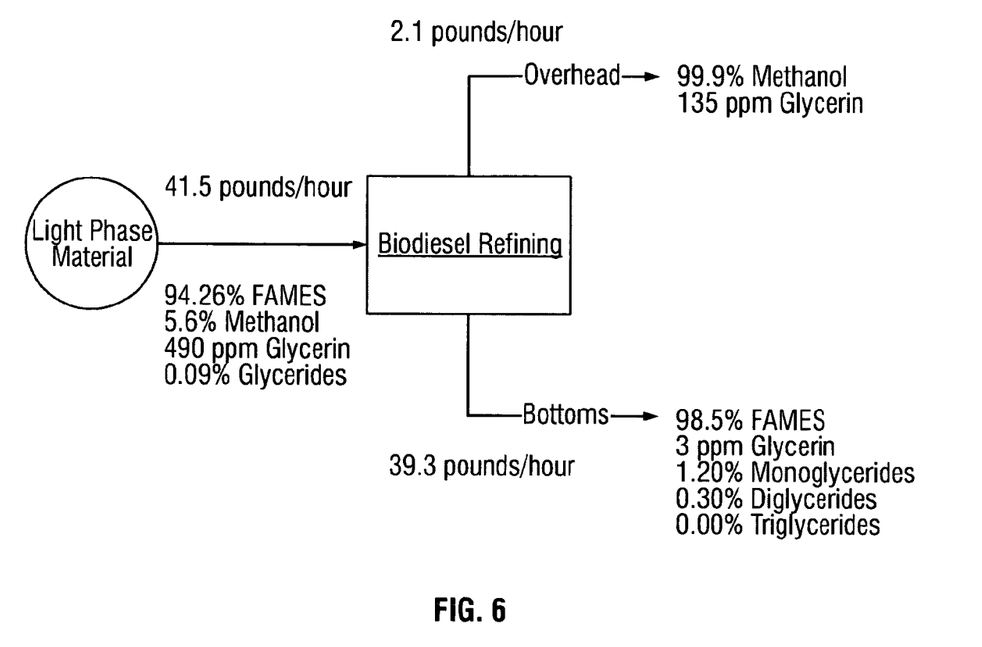
FIG. 6 is a schematic block diagram which demonstrates reactive distillation of a fatty acid alkyl ester rich stream upon separation from the transesterification effluent stream, as set forth in Example No. 6.

In a preferred embodiment, the fatty acid alkyl ester rich stream is subjected to reactive distillation to separate the fatty acid alkyl ester rich stream into a bottoms fraction, an overhead fraction (principally comprising excess alcohol) and a fatty acid alkyl ester product stream. Such separation utilizes the differences in the vapor pressures of the components of the fatty acid alkyl ester rich stream and the reactive loss of glycerin. The conditions in the distillation or fractionation column including temperature and pressure conditions, simultaneously with and in the same vessel wherein the said separation occurs, promote a chemical reaction to occur. Reactive distillation in the embodiment depicted in FIG. 6 decreases the concentration of glycerin and increases the amount of glycerides exiting the column. Thus, reactive distillation increases the efficiency of the production process.

The end result of reactive distillation is that the amount of glycerin seen in the transesterification effluent stream, or the first liquid phase, is greater than the total amount of glycerin which exits the distillation or fractionation column. This is attributable to the reaction of the glycerin with free fatty acids and or fatty acid alkyl esters in the reactive distillation column to form glycerides.

Preferably, the overhead fraction produced by the fatty acid alkyl ester distillation column is a (first) alcohol stream which comprises essentially the alcohol. Preferably the bottoms fraction comprises impurities having a high boiling point, unsaponifiable materials, monoglycerides, diglycerides, triglycerides and fatty acids. Preferably, the fatty acid alkyl ester product produced by the fatty acid alkyl ester distillation column meets ASTM specification D 6751.

Preferably, the fatty acid alkyl ester distillation column or fractionation column is operated at a pressure below about 2 pounds per square inch absolute. More preferably, the fatty acid alkyl ester distillation column or fractionation column is operated at a pressure in the range of about 0.1 pounds per square inch absolute to about 2 pounds per square inch absolute. Preferably, the fatty acid alkyl ester distillation column or fractionation column is operated at a temperature in the range of about 180° C. to about 280° C., more preferably between from about 180° C. to about 230° C. Preferably, the fatty acid alkyl ester distillation column or fractionation column contains a packing material.

The glycerin rich second liquid phase stream may further be purified and alcohol recovered from it. The recovered alcohol is operative to produce a purified glycerin product and a (second) wet alcohol stream. In a preferred embodiment, this step employs one or more of glycerin fractionation (wherein the fractions within the glycerin rich stream are separated by distillation), phase separation (wherein the impurities that co-fractionate with glycerin are removed by immiscibility and differences in density) and glycerin polishing (wherein other impurities are removed from glycerin).

The glycerin rich stream may further be subjected to phase separation wherein a fatty acid alkyl ester rich liquid phase and a glycerin rich liquid phase are separated and the two liquid phases may then be subject to purification as described in the paragraphs above.

The glycerin rich stream may further be purified in a glycerin distillation or fractionation column to produce a bottoms material, a side stream and an overhead stream. Preferably, the bottoms material contains essentially waste materials; the side stream contains essentially glycerin and trace impurities; and the overhead stream contains essentially alcohol and water that is collected for further purification and recycled.

Preferably, the glycerin distillation column is operated at an elevated temperature between about 180° C. and about 280° C., more preferably between from about 180° C. to about 230° C. The distillation column is typically operated at a reduced pressure, of below about 2 pounds per square inch absolute, typically the pressure is in the range of about 0.1 pounds per square inch absolute to about 2 pounds per square inch absolute.

The glycerin rich stream may further be subjected to a decolorization column wherein colored impurities and odors are removed from the glycerin, i.e., "glycerin polishing". The decolorization column typically comprises a packed bed of activated carbon operated at a temperature in the range of about 35° C. to about 200° C., preferably between from about 40° C. to about 100° C. The contact time is generally less than four hours. Activated carbon fines carried through the packed bed are removed by filtration.

Water may further be removed from the wet alcohol streams to render purified alcohol by subjecting the wet alcohol stream to an alcohol distillation or fractionation column at a temperature in the range of about 60° C. to about 110° C. and at a pressure in the range of about 14 pounds per square inch absolute to about 20 pounds per square inch absolute. Preferably, this purification comprises adsorption onto molecular sieves that can then be dried and reused or distillation resulting in a bottoms product consisting mainly of water.

At least a portion of the purified glycerin product may then be returned to the glycerolysis reactor for reaction with free fatty acids in the feedstock; at least a portion of the purified alcohol being recycled into the transesterification reactor for reaction with glycerides.

It is typically desired to neutralize the fatty acid alkyl ester and glycerin produced in the transesterification reactor. Neutralization is often required in light of the caustic conditions which characterize transesterification. Such neutralization may occur by addition of an acid to the transesterification effluent stream or to either the fatty acid alkyl ester rich stream or glycerin rich stream after such streams are separated from the transesterification effluent stream. Suitable acid treatments include mineral or more preferably organic acid treatments.

Figure 4:
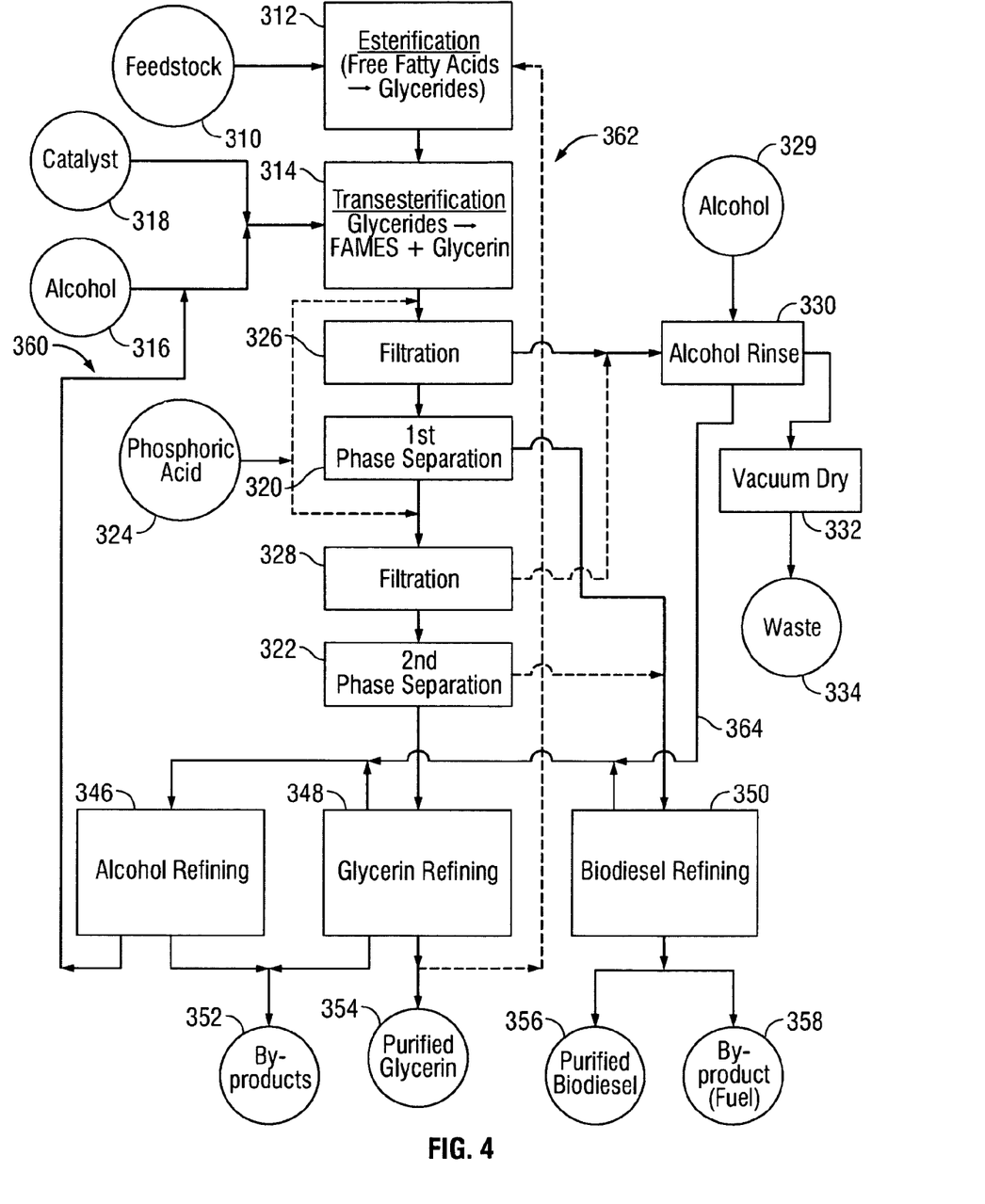
FIG. 4 is a schematic flow diagram of the process of the invention wherein a mineral acid is used in the neutralization of the alkali catalyst used during transesterification.

Suitable mineral acids include sulfuric acid and phosphoric acid. Reaction of the alkali catalyst with a mineral acid renders an insoluble salt that is removed from the glycerin rich stream in a solids separation operation. FIG. 4 is illustrative of the process wherein a mineral acid, such as phosphoric acid, is employed. In particular, FIG. 4 illustrates introduction of feedstock 310 containing free fatty acids into glycerolysis reactor 312 wherein the free fatty acids are converted to glycerides by esterification. The glycerides are then introduced into transesterification reactor 314 with alcohol 316 and alkali catalyst 318 wherein the glycerides are transesterified to form fatty acid alkyl esters and glycerin.

The transesterification effluent stream is first separated in $1^{st}$ phase separation 320 into a fatty acid alkyl ester rich stream and a glycerin rich stream. Each of these streams may then be purified in $2^{nd}$ phase separation 322 in accordance with the processes described herein.

The neutralization acid, phosphoric acid, 324 is added either prior to $1^{st}$ phase separation 320 or subsequent to $1^{st}$ phase separation 320 of the transesterification effluent stream after the fatty acid alkyl ester rich stream and glycerin rich stream have been separated. Such alternative or combination ports of introduction of the acid into the process are represented by the dotted lines in FIG. 4.

Unfortunately, use of phosphoric acid renders an insoluble precipitate. The formation of the insoluble precipitate mandates the use of filter 326 and/or filter 328. Suitable filters include rotary vacuum drum filters, plate and frame presses as well as belt presses.

In addition to the use of a filtration unit, use of a mineral acid further requires the rinsing of the insoluble by-product salts in order to wash residual organic materials from them. Suitable solvents include $C_1$-$C_5$ alcohols, such as methanol. Illustrated in FIG. 4 is the introduction of alcohol solvent 329 for use as alcohol rinse 330 which removes organic residue from the filter cake. Vacuum dry 332 is then used to remove alcohol from the filter cake and to dry the purified salt which then exits the process as waste 334. The solvent may then be recovered as stream 364 for reuse in the process.

Preferably, the process comprises drying the insoluble salt in a dryer under conditions wherein the temperature of the dryer exceeds the boiling point of the solvent at the operating pressure of the dryer. The dryer may optionally be operated under a vacuum to improve the drying. The dryer may further include a condenser to recover the solvent for reuse.

FIG. 4 further illustrates the refining of alcohol, glycerin and biodiesel in alcohol refinery vessel 346, glycerin refinery vessel 348 and biodiesel refinery vessel 350, respectively. The alcohol typically exits the system as byproduct stream 352 or is recycled via 360 back to the transesterification reactor. Refined glycerin is isolated as purified glycerin 354 or may be recycled back at 362 to the glycerolysis reactor. The alkyl esters may further be purified to produce purified biodiesel 356 or may exit the system as byproduct 358 in the form of, for example, burner fuel.

It is more preferable to employ an organic acid versus a mineral acid, however. While there are inorganic acids that don't create precipitating salts upon neutralization with the transesterified stream, all suffer from serious disadvantages. For instance, hydrochloric and perchloric acid produce chlorides in the process streams which, in turn, cause undesirable corrosion of steel and stainless steel, especially at elevated temperatures. Sulfuric acid, sulfurous acid and hydrogen sulfide suffer serious disadvantages due to the presence of sulfur which increases the tendency of sulfur to exit with the final biodiesel product. This, in turn, causes potential failure of sulfur level limits and the formation of unwanted sulfur oxide in emissions from biodiesel-burning engines. Arsenic acid, chromic acid, hydrocyanic acid and hydrofluoric acid are undesirably hazardous to use and/or require unwanted additional treatment methods for the disposal of undesirable byproducts. Lastly, iodic acid does not produce undesirable precipitates, but it is economically not viable.

When an organic acid is used, no insoluble salt is formed and thus it is unnecessary to subject the stream to any solids separation operation. Suitable organic acid include weak organic acids, such as formic acid, acetic acid and propionic acid. In such instances, the pH of the glycerin rich stream resulting from transesterification may first be adjusted below 8.0, preferably between from about 6.5 to about 7.0.

Figure 5:
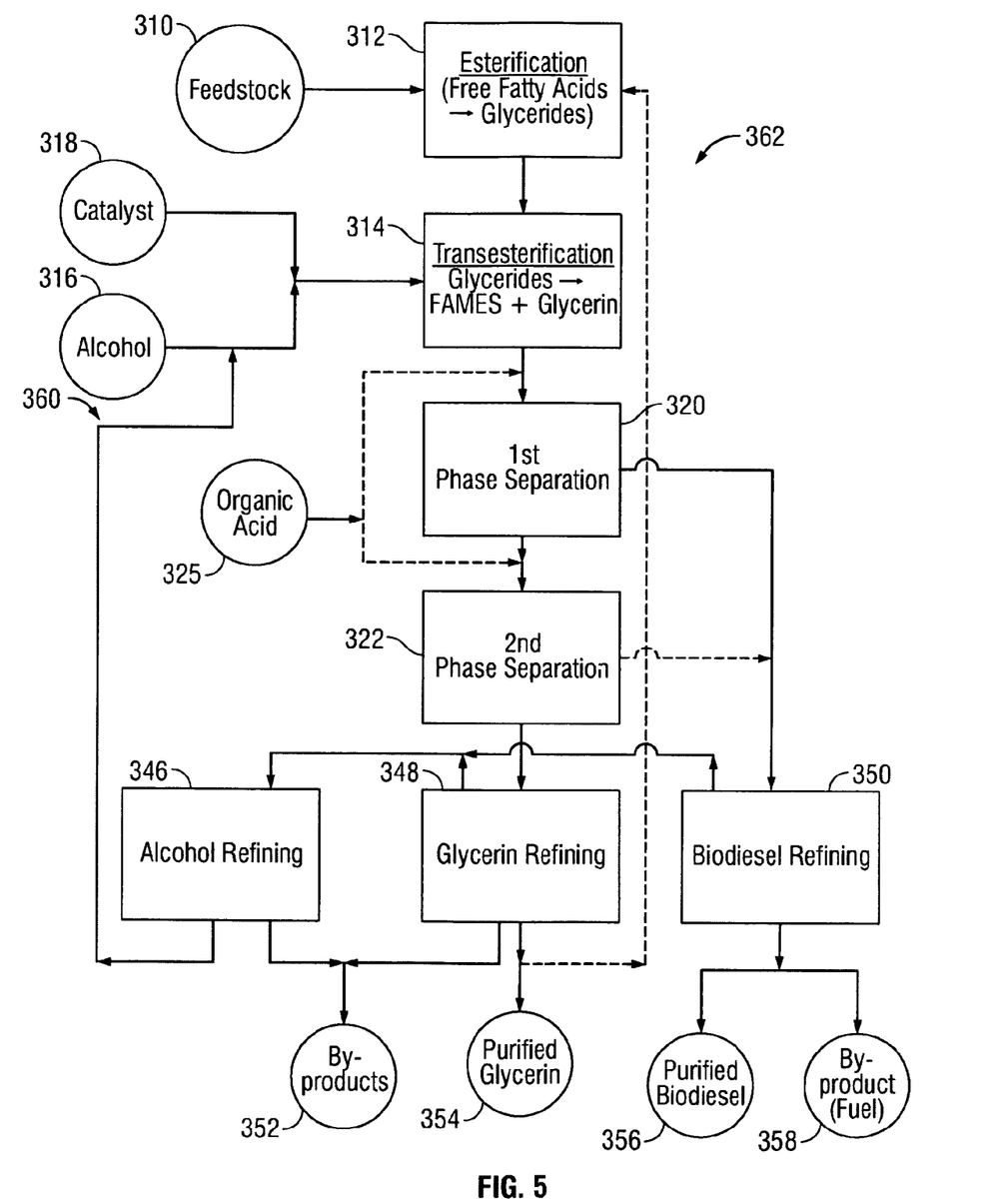
FIG. 5 is a schematic flow diagram of the process of the invention wherein an organic acid is used in the neutralization of the alkali catalyst used during transesterification.

FIG. 5 contrasts the inventive process wherein an organic acid 325 is used in the neutralization of the alkali catalyst versus a mineral acid. The use of an organic acid renders the steps of filtration, rinsing of the filter cake and vacuum drying unnecessary and thus offers advantages over the use of the mineral acid.

A system may be constructed in accordance with the teachings set forth herein for the production of biodiesel from a feedstock, such as a lipid feedstock having free fatty acids. The system may include:

(1) an optional conditioning reactor which is operative to continuously convert the feedstock to a conditioned feedstock. The conditioning reactor is operative to heat, mix and filter the feedstock in order to produce a conditioned feedstock;

(2) an optional system for continuously measuring the concentration of the free fatty acid in the conditioned feedstock. Suitable systems include an in-line free fatty acid titration device which is operative to quantify the concentration of the free fatty acid in the conditioned feedstock;

(3) a glycerolysis reactor wherein the free fatty acid in the feedstock is continuously reacted with glycerin to produce a glyceride. This reaction may be in response to a signal from the in-line free fatty acid titrator;

(4) a transesterification reactor for continuously reacting the glyceride with an alcohol and which is operative to convert the glyceride to a fatty acid alkyl ester and glycerin, preferably by an alkali catalyzed reaction. This reaction may proceed in response to the signal from the in-line free fatty acid;

(5) a separator for continuously separating the fatty acid alkyl ester from the glycerin and which is operative to produce a fatty acid alkyl ester rich stream and a glycerin rich stream. Suitable separators include a clarifier or a phase separation centrifuge which is operative to produce a (first) liquid phase in which the fatty acid alkyl ester is concentrated and a (second) liquid phase in which glycerin is concentrated.

(6) a purifier for continuously purifying the fatty acid alkyl ester rich stream and recovering the alcohol from the fatty acid alkyl ester rich stream; the purifier being operative to produce a purified biodiesel product and a first wet alcohol stream. Suitable purifiers include fractionation and distillation columns. In a preferred embodiment, the fatty acid alkyl ester rich stream is purified by reactive distillation;

(7) a purifier for continuously purifying the glycerin rich stream and recovering alcohol from the glycerin rich stream; the purifier being operative to produce a purified glycerin product and a second wet alcohol stream. Suitable purifiers include fractionation and distillation columns, including reactive distillation;

(8) a purifier for continuously purifying the wet alcohol streams that is operative to produce a purified alcohol product. Suitable purifiers include an alcohol fractionation column for treating the alcohol streams; and (9) pathways for recycling at least a portion of the purified glycerin product to the glycerolysis reactor and recycling at least a portion of the purified alcohol into the transesterification reactor for continuously reacting with the glyceride.

Figure 1:
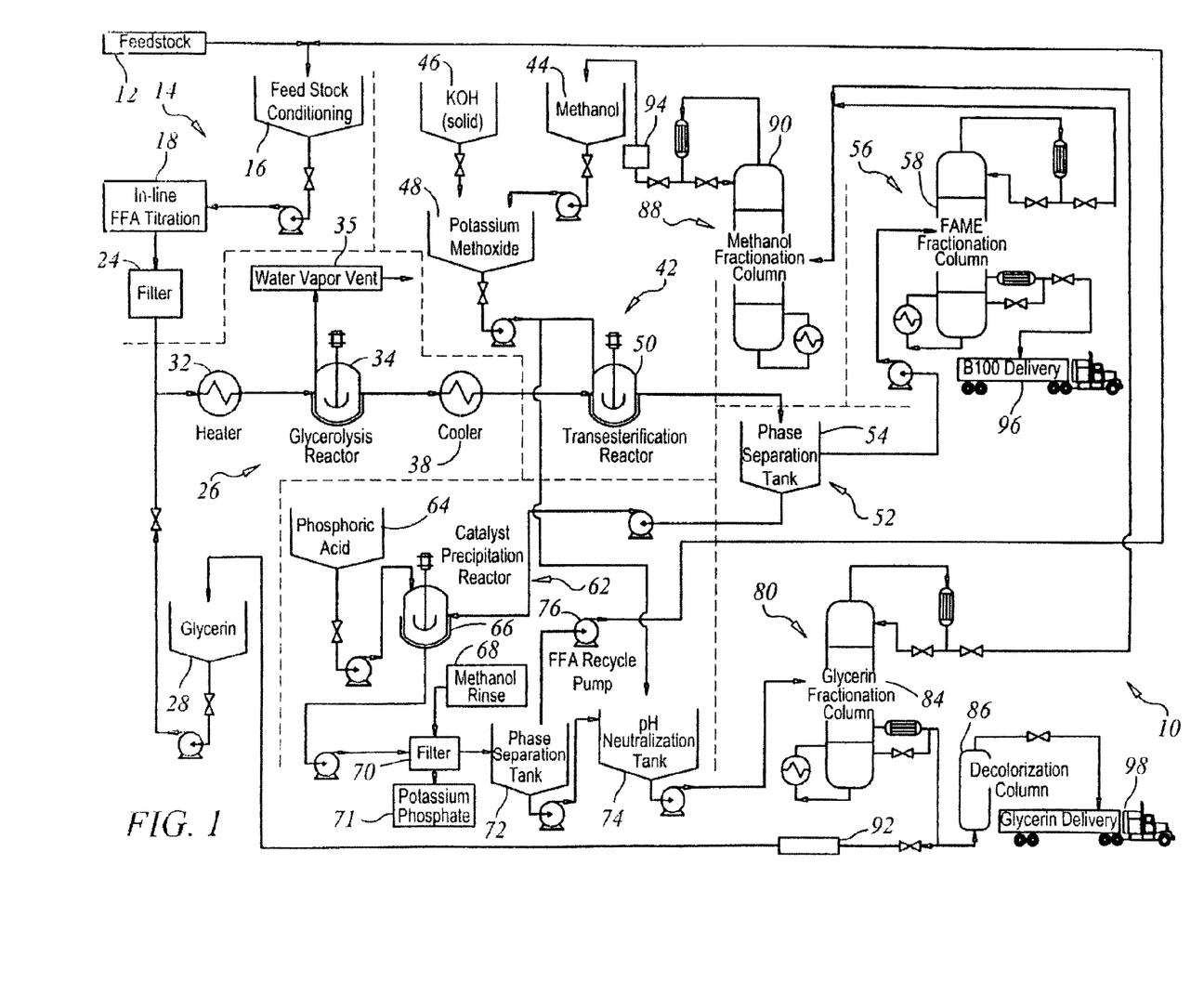
FIG. 1 is a schematic flow diagram of the process of the invention.

Referring to FIG. 1, a preferred embodiment of a biodiesel production process 10 for the conversion of high free fatty acid feedstocks into biodiesel is presented.

In feedstock introduction step 12, the feedstock is introduced to process 10. The introduced feedstock is preferably conditioned in feedstock conditioning operation 14 wherein feedstock is heated and mixed in conditioning reactor 16; the high free fatty acid feedstock being heated and mixed to ensure a uniform mixture. The free fatty acid may be quantified, such as in an in-line free fatty acid titration 18, wherein the concentration of free fatty acids in the feedstock is measured. In a first separation, solid (insoluble) substances are removed in filter 24.

The feedstock may include at least one free fatty acid at a concentration in the range of about 3 percent to about 97 percent by weight; moisture, impurities and unsaponifiable matter at a concentration up to about 5 percent by weight; and a remainder that includes monoglycerides, diglycerides and/or triglycerides. The feedstock may further include trap grease.

Preferably, the conditioning step is carried out and produces a conditioned feedstock with a temperature in the range of about 35° C. to about 250° C. and more preferably in the range of about 45° C. to about 65° C. In a preferred embodiment, the feedstock is heated to a temperature in the range of about 55° C. to about 65° C. Preferably, the resulting conditioned feedstock is substantially free of insoluble solids.

The conditioned feedstock is introduced to a glycerolysis reaction at 26 which preferably comprises glycerin addition step 28, heating step 32, glycerolysis step 34 in which free fatty acids are converted to glycerides and glycerolysis effluent cooling step 38.

Preferably, glycerolysis reaction step 26 further comprises performing the glycerolysis reaction at a temperature in the range of about 150° C. to about 250° C.; and removing water from the environment of the glycerolysis reaction. More preferably, glycerolysis reaction step 26 further comprises using two or more continuous stirred tank reactors in series.

In a preferred embodiment the free fatty acid and glycerin are continuously reacted, typically in the absence of a catalyst, in a glycerolysis reactor at a temperature of about 220° C. and at a pressure of about 2 pounds per square inch absolute, in an esterification reaction to produce an effluent stream that contains less than 0.5 percent by weight of free fatty acids and a plurality of glycerides. Preferably, the purified glycerin product is continuously added to the glycerolysis reactor at a rate in the range of about 35 percent to about 400 percent of the stoichiometric amount of free fatty acids and water is continuously removed from the glycerolysis reactor as a vapor in water venting step 35 through a fractionation column that returns condensed glycerin to the glycerolysis reactor.

Preferably, the glycerolysis reactor 34 comprises at least two continuous stirred tank reactors that are operated in series, the reactors having a combined residence time of not greater than about 400 minutes for feedstock with a 20 percent by weight free fatty acid concentration.

Water is preferably removed as vapor through a fractionation column or a distillation column that returns condensed glycerin to the glycerolysis reactor.

The effluent from glycerolysis reaction step 26 is introduced to alkali catalyzed transesterification reaction at 42 which preferably comprises alcohol metering step 44, catalyst metering step 46, alkoxide addition step 48 and transesterification step 50 wherein the glycerides undergo transesterification in the transesterification reactor.

In transesterification step 50, glycerides are contacted with an effective amount of alcohol and an effective amount of alkali catalyst under conditions wherein the glycerides, alcohol and alkali catalyst come into substantially intimate contact. Preferably, the alkali catalyst is selected from the group consisting of sodium hydroxide and potassium hydroxide.

The transesterification reaction step 42 is preferably conducted at a temperature in the range of about 20° C. to about 65° C. and at an absolute pressure in the range of about 14.5 psia. More preferably, transesterification reaction step 42 comprises conducting the transesterification at a temperature in the range of about 25° C. to about 65° C. and at an absolute pressure near atmospheric. In a preferred embodiment, the alcohol and alkali catalyst are mixed at prescribed rates prior to their addition to the transesterification reaction operation.

In a preferred embodiment, transesterification reaction step 42 comprises reacting the plurality of glycerides contained in the glycerolysis effluent stream with an alcohol in the transesterification reactor. In the transesterification reactor, the plurality of glycerides are preferably mixed with the alcohol and alkali catalyst by an agitator and continuously reacted with the alcohol.

Preferably, the alcohol, most preferably methanol, is added to the transesterification reactor at a rate equal to about 200 percent of the stoichiometric amount of alcohol required for the catalyzed reaction and the alkali catalyst is added to the transesterification reactor at a rate of about 0.5 percent by weight to 2.0 percent by weight of glycerides present in the glycerolysis effluent stream. More preferably, the alkali catalyst is dissolved in the alcohol prior to their introduction to the transesterification reactor.

Preferably, the transesterification reactor comprises at least two continuous stirred tank reactors that are operated in series, said reactors having a combined residence time of not more than about 90 minutes.

The transesterification reactor effluent stream contains a plurality of fatty acid alkyl esters and glycerin. The effluent from transesterification reaction step 42 is preferably introduced to second separation at 52 in which a light phase (for instance, specific gravity 0.69-0.88) is separated from a heavy phase (for instance, specific gravity 0.90-1.20). In biodiesel purification step (operation) 58, excess methanol and high-boiling impurities are preferably separated from fatty acid alkyl esters in the light phase and the alcohol is collected for reuse. Preferably, separating the fatty acid alkyl esters from the glycerin involves using the density difference between the first light liquid phase and the second heavy liquid phase to separate them.

In biodiesel purification step 56, differences in component vapor pressures are used to separate excess alcohol and high-boiling impurities from fatty acid alkyl esters in the light phase, and the alcohol is collected for reuse.

In a preferred embodiment, second separation step 52 comprises separating the fatty acid alkyl esters from the glycerin in the transesterification effluent stream in a continuous clarifier in phase separation step 54. Preferably, in the continuous clarifier, a first light liquid phase in which the plurality of fatty acid alkyl esters are concentrated and a second heavy liquid phase in which glycerin is concentrated are continuously separated at a temperature of about 25° C. to about 65° C. to produce a fatty acid alkyl ester rich stream and a glycerin rich stream.

Alternatively, the separation step may be a reactive distillation or fractionation column wherein the fatty acid alkyl ester and glycerin may be separated. The transesterification effluent stream entering the reactive column contains, in addition to fatty acid alkyl esters, a certain amount of glycerin, glycerides and unreacted or non-convertible lipid feedstock. In the reactive column, some of the glycerin reacts with unreacted fatty acids and/or fatty acid alkyl esters to form glycerides.

In preferred embodiments, the light phase is separated in fatty acid alkyl esters purification step 56. In step 56, differences in component vapor pressures are used to separate excess alcohol and high-boiling impurities from fatty acid alkyl esters in the first liquid phase, and the alcohol is collected for reuse.

Preferably, purifying the fatty acid alkyl ester rich stream step 58 further comprises using a distillation column to separate the fatty acid alkyl ester rich stream into a bottoms fraction, an overhead fraction comprising primarily the alcohol, and a side stream fraction comprising a fatty acid alkyl ester product. Preferably, the bottoms fraction produced by the distillation column comprises impurities, unsaponifiable materials, monoglycerides, diglycerides, triglycerides and free fatty acids. Preferably, the fatty acid alkyl ester product produced by the distillation column meets ASTM specification D 6751. Preferably, the overhead fraction produced by the distillation column comprises essentially the alcohol.

Preferably, the distillation column is operated at a pressure below about 2 pounds per square inch absolute and at a temperature in the range of about 180° C. to about 280° C. More preferably, the distillation column is operated at a pressure in the range of about 0.1 pounds per square inch absolute to about 1 pound per square inch absolute and at a temperature in the range of about 180° C. to about 230° C. Preferably, the distillation column contains packing material that is operative to achieve high efficiency vacuum distillation. More preferably, the distillation column is packed with a structured packing.

In preferred embodiments, the heavy phase from second separation step 52 is treated in catalyst separation step 62 comprising mineral acid addition step 64, catalyst precipitation step 66 in which the alkali catalyst is reacted with a mineral acid to produce a solid precipitate, catalyst precipitation reactor effluent filtration step 70 in which an alcohol washing step 68 occurs before the alkali salt precipitate is removed in salt recovery step 71, filtrate separation step 72 in which the precipitate-free filtrate is separated into two liquid phases, with the fatty acids and fatty acid alkyl esters floating to the top and the glycerin and most of the alcohol sinking to the bottom, pH neutralization step 74 in which the pH of the glycerin is increased, and free fatty acid recycling step 76.

Crude glycerin may be treated in glycerin purification step 80 wherein glycerin is purified by differences in component vapor pressures. A preferred embodiment comprises distillation or fractionation step 84 in which the alcohol and high boiling impurities are separated from the glycerin. Glycerin decolorization step 86 comprises using a packed bed of activated carbon to remove color and odor from the distilled glycerin.

Preferably, in purifying the glycerin rich stream and recovering alcohol from it to produce the purified glycerin product and a wet alcohol stream, the alkali catalyst in the glycerin rich stream is reacted with a mineral acid, such as phosphoric acid or sulfuric acid, to produce an insoluble salt having fertilizer value that is removed from the glycerin rich stream in a solids separation operation and thereafter filtered and rinsed with the alcohol.

The pH of the glycerin rich stream is adjusted to about neutral by adding a caustic alkali solution and then further purified in a glycerin distillation column that is operated at a temperature in the range of about 180° C. to about 230° C. and at a pressure below about 1 pound per square inch absolute and in a decolorization column comprising a packed bed of activated carbon operated at a temperature in the range of about 40° C. to about 200° C.

In a more preferred embodiment, the pH of the glycerin rich stream is adjusted to between about 6.5 and 8.0 by the addition of an acid. An organic acid, such as a weak organic acid, like acetic acid, propionic acid or formic acid, is then introduced to the glycerin rich stream. Salts present in the glycerin rich stream remain soluble. Thus, filtering and rinsing steps are unnecessary by use of the organic acid.

Preferably, the wet alcohol is treated in alcohol purification step 88 in which water is removed from the wet alcohol. More preferably, the water is removed by vapor pressure differences or adsorption. In a preferred embodiment, the alcohol is purified by distillation or fractionation in alcohol distillation or fractionation step 90. In a preferred embodiment, purifying the wet alcohol stream comprises removing water from it to produce a purified alcohol product. Preferably, the wet alcohol stream is purified in an alcohol distillation column that is operated at a temperature in the range of about 60° C. to about 110° C. and at a pressure in the range of about 14 pounds per square inch absolute to about 20 pounds per square inch absolute.

In glycerin recycling step 92, glycerin is preferably recycled to step 28 and in alcohol recycling step 94, alcohol is preferably recycled to step 44. Preferably, glycerin recycling step 92 involves recycling at least a portion of the purified glycerin product into the glycerolysis reactor for reaction with the plurality of free fatty acids in the feedstock. Preferably, the alcohol recycling step involves recycling at least a portion of the purified alcohol product into the transesterification reactor for reaction with the plurality of glycerides. The additional alcohol required for the transesterification reaction is supplied to the alkoxide tank. Biodiesel is delivered to its market in biodiesel delivery step 96 and glycerin is delivered to its market in glycerin delivery step 98.

Figure 2:
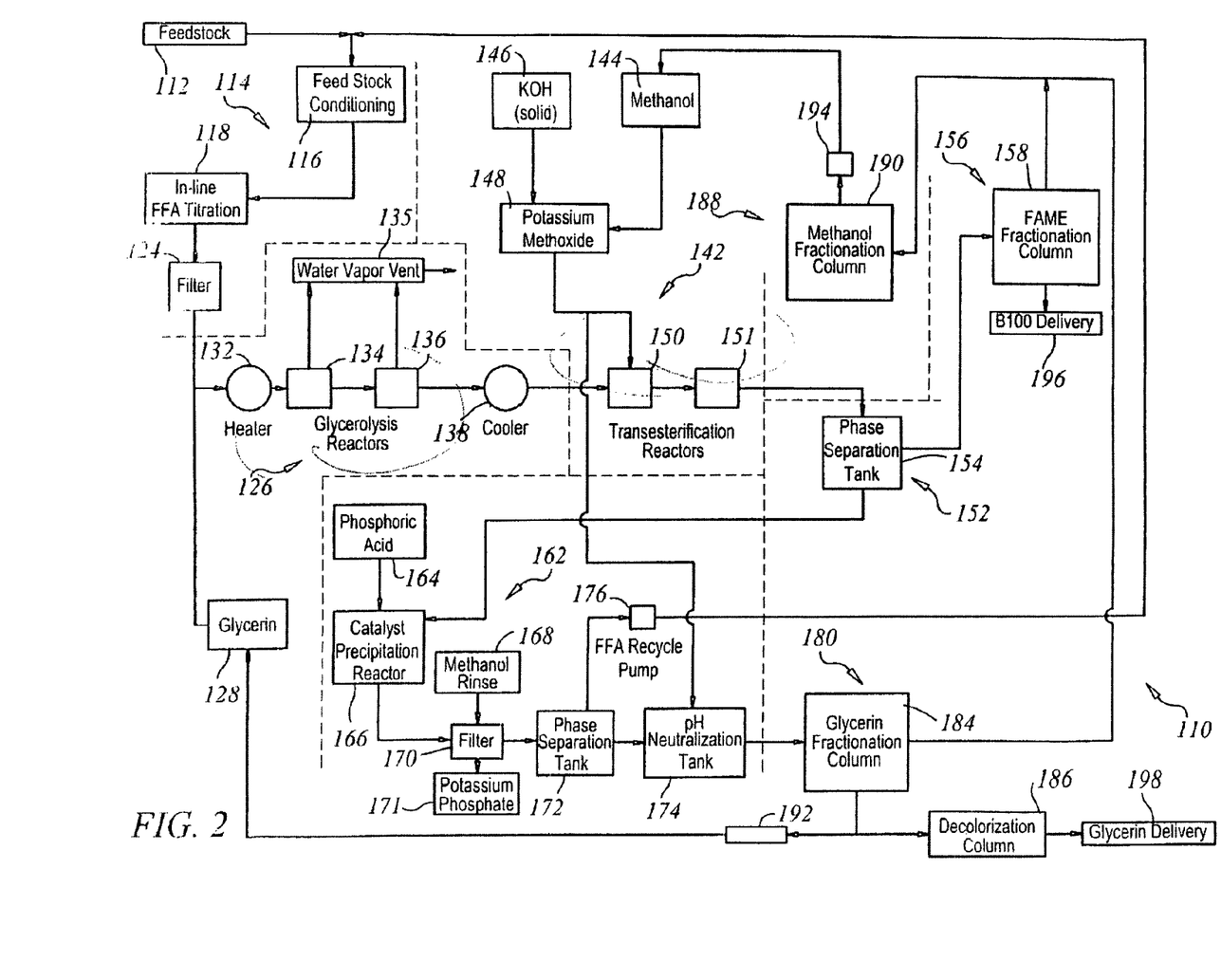
FIG. 2 is a schematic block diagram of the biodiesel production system in accordance with the invention.

Referring to FIG. 2, a preferred embodiment of system 110 for the conversion of high free fatty acid feedstocks into biodiesel is presented. Biodiesel production system 110 preferably comprises the subsystems and reactors described below wherein the alcohol employed is methanol.

In feedstock introduction subsystem 112, the feedstock is introduced to system 110. In a preferred embodiment, the feed material is composed of between 0 and 100 percent free fatty acid content, with the remainder comprising mono-, di- and triglycerides, moisture, impurities and unsaponifiables (MIU).

The introduced feedstock may optionally be conditioned in feedstock conditioning subsystem 114 comprising feedstock heating and mixing vessel 116 in which the high free fatty acid feedstock is heated and mixed to ensure a uniform, homogeneous mixture with uniform viscosity. The concentration of free fatty acids in the feedstock may be measured by in-line titration device 118. The concentration is measured continuously to allow continuous control of downstream process steps.

Preferably, the feed material is heated in feedstock heating and mixing vessel 116 to ensure that all of the available lipids are liquid and that solids are suspended. Temperatures in the range of at least 35° C. but not more than 200° C. are adequate to melt the lipids, decrease their viscosity and allow thorough mixing of the feedstock. A jacketed stirred tank may be used to provide agitation and maintain the feedstock at increased temperature.

The conditioned feedstock may then be introduced to glycerolysis reaction subsystem 126 which comprises glycerin addition apparatus 128, input heater 132, first glycerolysis reactor 134 and second glycerolysis reactor 136 and glycerolysis effluent cooler 138. The filtered product of step 24 is combined with glycerin and subjected to conditions that promote the glycerolysis reaction in glycerolysis reaction subsystem 126. In a preferred embodiment, these conditions include a reaction temperature between from about 150° C. to about 250° C. and a pressure between about 0.1 pounds per square inch, absolute (psia) and about 30 psia. A more preferred condition is a temperature of about 220° C. and a pressure of about 2 psia.

Glycerin is added to the filtered grease feedstock in excess of the free fatty acid molar quantity of the grease feedstock. This excess is in the range of 10 percent to 300 percent excess glycerin (from 110 percent to 400 percent of the stoichiometric amount). In this embodiment, the glycerolysis reactors used as elements 134 and 136 are configured as two heated, continuous stirred tank reactors in series. In these vessels, the mixture of glycerin and grease (containing free fatty acids) is agitated to keep the two immiscible fluids in intimate contact.

In a preferred embodiment, mixing is provided by an agitator. Under these conditions, the free fatty acids are converted into glycerides (mono-, di-, or triglycerides) with the production of water. The water is vented as vapor and removed from the system together with any water that was initially present in the feedstock in water vapor vent 135. The free fatty acid content of the reactor effluent stream in this preferred embodiment of the invention can consistently be maintained at less than 0.5 percent w/w.

Because of the corrosive nature of free fatty acids, the glycerolysis reactor is preferably constructed of materials resistant to organic acids.

The effluent from glycerolysis reaction subsystem 126 contains mono-, di-, and triglycerides and residual fatty acids. The glycerolysis reaction effluent is introduced to alkali catalyzed transesterification subsystem 142 which preferably comprises methanol metering apparatus 144, potassium hydroxide metering apparatus 146, methoxide addition apparatus 148 and first transesterification reactor 150 and second transesterification reactor 151 in which the glycerides undergo transesterification.

In transesterification reaction subsystem 142, the glycerides are transesterified with an alkali catalyst and a simple alcohol having 1 to 5 carbons. In a preferred embodiment, the alkali catalyst is potassium hydroxide and the alcohol is methanol. The residual free fatty acids are saponified consuming a molar quantity of alkali catalyst about equal to the number of moles of free fatty acid present.

The transesterification reaction is preferably catalyzed by potassium methoxide, which is formed from the addition of potassium hydroxide to methanol. The amount of potassium hydroxide added is preferably equivalent to 0.5 percent to 2.0 percent w/w of the glycerides present in the feed solution. The methanol and catalyst are combined and added to the solution of glycerides coming from the glycerolysis reactors by methoxide addition apparatus 148.

A 200 percent stoichiometric excess of methanol based upon the molar concentration of glycerides is added to the reaction mixture. Upon entering each transesterification reactor 150 and 151, the two-phase system undergoes vigorous mixing.

Preferably, the reaction temperature is held between about 25° C. and about 65° C. At this temperature, the miscibility of the phases is limited and mixing is required to achieve a high conversion rate. The residence time required is dependent on glyceride composition of the feed (between mono-, di- and triglycerides), temperature, catalyst concentration and mass transfer rate.

Thus, agitation intensity is preferably considered in selecting a residence time. Typically, the residence time required for greater than (>) 99 percent conversion of glycerides to alkyl esters is 20 to 30 minutes.

In the transesterification reactor, the presence of potassium hydroxide, methanol, and fatty acid esters can be corrosive. In a preferred embodiment, at least two continuous stirred tank reactors in series are used. Suitable resistant materials are preferably chosen for the reactors.

The effluent from transesterification subsystem 142 may be introduced to phase separation subsystem 152 which comprise phase separation tank 154 in which a light phase (for instance, specific gravity 0.69-0.88) is separated from a heavy phase (for instance, specific gravity 0.90-1.2). The effluent streams from the phase separator are a light phase fatty acid alkyl esters comprised of methanol and alkyl esters (biodiesel), a fraction of the excess alcohol and some impurities, and a heavy phase (crude glycerin) containing glycerin, alcohol, FAAEs, soaps, alkali catalyst, a trace of water and some impurities.

Phase separation unit 154 is preferably a conventional liquid/liquid separator, capable of separating of the heavy phase from the light phase. Suitable phase separation units include commercially available equipment, including continuous clarifier 154.

In biodiesel purification subsystem 156, excess methanol and high-boiling impurities may be separated from the fatty acid methyl esters in the light phase in fractionation column 158 and methanol collected for reuse. Preferably, purifying the fatty acid methyl ester rich stream subsystem 156 further comprises a fatty acid alkyl ester distillation column 158 for separating the fatty acid alkyl ester rich stream into a bottoms fraction, an overhead fraction comprising primarily methanol, and a side stream fraction comprising a fatty acid alkyl ester product.

Preferably, the bottoms fraction produced by distillation column 158 comprises impurities, and unsaponifiable materials, monoglycerides, diglycerides, triglycerides and fatty acids. Preferably, the fatty acid methyl ester product produced by distillation column 158 in FIG. 2 meets ASTM specification D 6751.

Preferably, the overhead fraction produced by distillation column 158 comprises essentially methanol. Preferably, distillation column 158 is operated under pressure below about 2 pounds per square inch absolute and at a temperature in the range of about 180° C. to about 280° C. More preferably, distillation column 158 is operated under pressure in the range of about 0.1 pounds per square inch absolute to about 2 pounds per square inch absolute and at a temperature in the range of about 180° C. to about 230° C. Preferably, distillation column 158 contains high efficiency structured packing material.

The heavy phase separated in phase separation tank 154 is preferably treated in catalyst separation subsystem 162 comprising a mineral acid (such as phosphoric acid) addition apparatus 164, catalyst precipitation reactor 166, catalyst precipitation reactor effluent filter 170 in which washing with methanol 168 occurs before the potassium phosphate precipitate 171 is removed from the filter, filtrate separation tank 172, pH neutralization tank and free fatty acid recycling apparatus 176.

In catalyst separation subsystem 162, the crude glycerin phase is pumped to a catalyst precipitation reactor where a mineral acid 164 is added. Preferably, the amount of acid added is a molar quantity equal to the molar quantity of alkali catalyst used in the transesterification reaction. The product of the reaction is an insoluble salt that can be separated as a solid. In addition to forming an insoluble salt, the acid converts soaps formed in transesterification reaction subsystem 142 to free fatty acids.

In a preferred embodiment, potassium hydroxide is used as the transesterification catalyst, and the precipitation reaction uses phosphoric acid to form monobasic potassium phosphate. This salt is not soluble in this system and can be removed by simple filtration. As the potassium phosphate salt is filtered in catalyst precipitation reactor effluent filter 170, methanol 168 is used to wash glycerin and other process chemicals off of the precipitate.

The filtrate from catalyst precipitation reactor effluent filter 170 is sent to another phase separation operation where two liquid phases form and separate according to their relative specific gravities in filtrate separation tank 172. Glycerin, water, impurities and most of the methanol report to the bottom or heavy phase, while fatty acid alkyl ester, some alcohol and fatty acids report to the top, or light phase. The light phase is combined with the light phase from the previous phase separation subsystem (subsystem 152) and sent to the fractionation column 158. The heavy phase is sent to a reaction operation where any residual acid is neutralized in pH neutralization reactor 174 by adding a small amount of caustic. In a preferred embodiment, this is performed in a continuous stirred tank reactor.

Following pH neutralization reactor 174, the crude glycerin phase is sent to the glycerin refining subsystem 180, where the methanol and water are separated and collected for further purification and the glycerin is separated from the high boiling impurities. In a preferred embodiment, glycerin separation is performed in glycerin distillation or fractionation column 184 with a glycerin side draw. The distilled glycerin may further be treated in glycerin decolorization column 186 in which activated carbon is used to remove color and odor from the distilled glycerin.

The methanol recovered from the distillation column contains trace amounts of water and is therefore considered a "wet" methanol stream that must be purified prior to reuse in the process in methanol purification subsystem 188. This "wet" methanol stream is collected and purified by distillation in methanol purification column 190 before being pumped back into the inventory storage tanks.

The distilled glycerin stream is then subjected to decolorization and deodorization through activated carbon bed 186. The feed enters the column from the bottom and is allowed to flow upwards through the activated carbon bed resulting in a colorless, solventless and salt free glycerin that is >95 percent pure.

Glycerin recycling pump 192 may be used to recycle glycerin to glycerin addition apparatus 128. Methanol recycling apparatus 194 is preferably used to recycle methanol to methanol metering apparatus 144.

Biodiesel is then delivered to its market in biodiesel delivery vehicle 196 and glycerin is delivered to its market in glycerin delivery vehicle 198.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

EXAMPLES

Example No. 1

Rendered yellow grease with a free fatty acid concentration of 20 percent by weight and 2 percent moisture, impurities and unsaponifiables (MIU) was fed to continuous stirred tank glycerolysis reactors at 100 pounds per minute (lbs/min). The grease was filtered and titrated intermittently as it was fed to the glycerolysis reactor. Glycerin was added at a rate of 13 lbs/min. The temperature of the grease and glycerin mixture was raised to 210° C. as it was fed into the first of the glycerolysis continuous stirred tank reactors. In the reactor, the pressure was reduced to 2 psia and the temperature was maintained at 210° C. The vessel was fitted with a high intensity agitator to keep the immiscible liquids in contact. Water vapor produced by the reaction was removed through vents in the reactor headspace. The residence time in each of the glycerolysis reactors was 2.5 hours. The conversion of fatty acids to glycerides in the first vessel was 85 percent. The fatty acid concentration leaving the second reactor was maintained at 0.5 percent w/w.

The product from the glycerolysis reactors was cooled to 50° C. and fed continuously to the transesterification reactors in which a solution of potassium hydroxide in methanol was added. The potassium hydroxide was added at a rate of 1.1 lbs/min and mixed with 22 lbs/min of methanol. The transesterification took place in two continuous stirred tank reactors in series, each with a two-hour residence time.

The transesterified product was then fed to a phase separation tank where the majority of the fatty acid methyl esters, a small amount of unreacted glycerides and a small concentration of the unreacted methanol floated to the top. The glycerin, the majority of the unreacted methanol, some fatty acid methyl esters, potassium hydroxide and soaps sank to the bottom.

The bottom, or heavy phase was sent to an acidification reactor where the potassium hydroxide catalyst added in the transesterification step was reacted with 1.96 lbs/min phosphoric acid. The soaps converted to free fatty acids and the potassium hydroxide was neutralized. The product of this acidification was monobasic potassium phosphate, which was not soluble in this system.

The monobasic potassium phosphate precipitate was filtered out and the filtrate was fed to a second phase separation tank where the fatty acid methyl esters and free fatty acids present in the filtrate floated to the top and the glycerin and methanol sank to the bottom. The top, or light, phase was mixed with the light phase from the first phase separation tank and fed to the fatty acid methyl ester fractionation column. The pH of the heavy phase was adjusted back to 7.5 with potassium hydroxide and fed to the glycerin fractionation column.

The glycerin fractionation column recovered 10 lbs/min of methanol and 18 lbs/min of glycerin. The glycerin produced was more than 95 percent pure with non-detectable concentrations of salts and methanol. This glycerin stream was split into two streams: 13 lbs/min was recycled back to the glycerin feed tank for the glycerolysis reaction and 5 lbs/min was pumped through the decolorization column and collected for market.

The two light phase streams were fed to the fatty acid methyl ester fractionation column where 2 lbs/min of methanol was recovered and 92 lbs/min of fatty acid methyl esters meeting ASTM D 6751-02 (Standard Specification for Biodiesel Fuel (B100) Blend Stock for Distillate Fuels) were produced.

Example No. 2

Fancy bleachable inedible tallow with a free fatty acid concentration of 4 percent by weight and 0.5 percent MIU (moisture, impurities and unsaponifiables) was fed to a continuous stirred tank reactor at 100 lbs/min. The grease was filtered and titrated continuously as it was fed to the glycerolysis reactors. Glycerin was added at a rate of 2.6 lbs/min. The temperature of the grease and glycerin mixture was raised to 210° C. as it was fed into the first of the glycerolysis continuous stirred tank reactors. In the reactor the pressure was reduced to 2 psia and the temperature was maintained. The vessel was fitted with an agitator to keep the immiscible liquids in contact. Water vapor produced by the reaction was removed through vents in the reactor headspace. The residence time in each of the glycerolysis reactors was 2.5 hours. The conversion of fatty acids to glycerides in the first vessel was 92 percent. The fatty acid concentration leaving the second reactor was maintained at 0.5 percent by weight.

The product from the glycerolysis reactors was cooled to 50° C. and fed to the transesterification reactors in which a solution of potassium hydroxide in methanol was added. The potassium hydroxide was added at a rate of 1.0 lbs/min and mixed with 22 lbs/min of methanol. The transesterification took place in two continuous stirred tank reactors in series, each with a two-hour residence time.

The transesterified product was then fed to a phase separation tank where the majority of the fatty acid methyl esters and a small concentration of the unreacted methanol floated to the top. The glycerin, the majority of the unreacted methanol, some fatty acid methyl esters, potassium hydroxide and soaps sank to the bottom.

The bottom, or heavy phase was sent to an acidification reactor where the potassium hydroxide catalyst added in the transesterification operation was reacted with 1.79 lbs/min phosphoric acid. The soaps converted back to free fatty acids and the potassium hydroxide was neutralized. The product of this acidification was monobasic potassium phosphate, which was not soluble in this system.

The monobasic potassium phosphate precipitate was filtered out and the filtrate was fed to a second phase separation tank where the fatty acid methyl esters and free fatty acids floated to the top and the glycerin and methanol sank to the bottom. The top, or light, phase was mixed with the light phase from the first phase separation tank and fed to the fatty acid methyl ester fractionation column. The pH of the heavy phase was adjusted to 7.8 with 0.1 lbs/min potassium hydroxide and fed to the glycerin fractionation column.

The glycerin fractionation column recovered 10 lbs/min of methanol and 10.2 lbs/min of glycerin. The glycerin produced was more than 95 percent pure with non-detectable concentrations of salts and methanol. The glycerin stream was split into two streams: 2.6 lbs/min was recycled back to the glycerin feed tank for the glycerolysis reaction and 7.6 lbs/min was collected for market.

The two light phase streams were fed to the fatty acid methyl ester fractionation column in which 2.1 lbs/min of methanol was recovered and 93 lbs/min of fatty acid methyl esters meeting ASTM D 6751-02 (Standard Specification for Biodiesel Fuel (B100) Blend Stock for Distillate Fuels) was produced.

Example No. 3

Degummed, food-grade soybean oil with a free fatty acid concentration of 0.5 percent by weight and 0.5 percent MIU (moisture, impurities and unsaponifiables) was fed to a conditioning chamber at 100 lbs/min. The grease was filtered and titrated continuously as it was transferred from the feedstock conditioner. Due to the low concentration of free fatty acids, the glycerolysis section of the process was bypassed when using this feedstock.

The fatty acid concentration entering the transesterification reactors was 0.5 percent by weight. The potassium hydroxide was added at a rate of 1.0 lbs/min and mixed with 22 lbs/min of methanol. The transesterification took place in two continuous stirred tank reactors in series, each with a two-hour residence time.

The transesterified product was then fed to a phase separation tank where the majority of the fatty acid methyl esters and a small concentration of the unreacted methanol floated to the top. The glycerin, the majority of the unreacted methanol, some fatty acid methyl esters, potassium hydroxide and soaps sank to the bottom.

The bottom, or heavy, phase was sent to an acidification reactor where the potassium hydroxide catalyst added in the transesterification operation was reacted with 1.76 lbs/min phosphoric acid. The pH of the solution was decreased, and the product of this acidification was monobasic potassium phosphate, which was not soluble in this system.

The precipitate was filtered out at 2.2 lbs/min and the filtrate was fed to a phase separation tank in which the fatty acid methyl esters and free fatty acids floated to the top and the glycerin and methanol sank to the bottom. The top, or light, phase was mixed with the light phase from the first phase separation tank and fed to the fatty acid methyl ester fractionation column. The heavy phase was transferred to another tank and the pH was adjusted to 7.4 with 0.1 lbs/min potassium hydroxide. Then, the glycerin/methanol mixture was fed to the glycerin fractionation column.

The glycerin fractionation column recovered 10 lbs/min of methanol and 8.5 lbs/min of glycerin. The glycerin produced had a purity greater than 95 percent with non-detectable concentrations of salts and methanol. The glycerin was collected for market.

The two light phase streams were fed to the fatty acid methyl ester fractionation column where 2.1 lbs/min of methanol was recovered and 93 lbs/min of fatty acid methyl esters meeting ASTM D 6751-02 (Standard Specification for Biodiesel Fuel (B100) Blend Stock for Distillate Fuels) were produced.

Example No. 4

Rendered trap grease with a free fatty acid concentration of 68 percent by weight and 5% MIU (moisture, impurities and unsaponifiables) was fed to the invention at 100 lbs/min. The grease was filtered and titrated continuously as it was fed to the glycerolysis reactors. Glycerin was added at a rate of 44 lbs/min. The temperature of the grease and glycerin mixture was raised to 210° C. as it was fed into the first of the glycerolysis continuous stirred tank reactors. In the reactor, the pressure was reduced to 2 psia and the temperature was maintained. Water vapor produced by the reaction was removed through vents in the reactor headspace. The residence time in each of the glycerolysis reactors was 3.5 hours. The conversion of fatty acids to glycerides in the first vessel was 87 percent. The fatty acid concentration leaving the second reactor was maintained at 0.5 percent by weight.

The product from the glycerolysis reactors was cooled to 50° C. and fed to the transesterification reactors where a solution of potassium hydroxide in methanol was added. The potassium hydroxide was added at a rate of 1.4 lbs/min and mixed with 21 lbs/min of methanol. The transesterification took place in two continuous stirred tank reactors in series, each with a two-hour residence time.

The transesterified product was then fed to a phase separation tank where the majority of the fatty acid methyl esters and 10 percent of the unreacted methanol floated to the top and the glycerin, the majority of the unreacted methanol, some fatty acid methyl esters, potassium hydroxide and soaps sank to the bottom.

The bottom, or heavy, phase was sent to an acidification reactor where the potassium hydroxide catalyst added in the transesterification operation was reacted with 2.45 lbs/min phosphoric acid. The soaps converted back to free fatty acids and the potassium hydroxide was neutralized. The product of this acidification was monobasic potassium phosphate, which was not soluble in this system.

The monobasic potassium phosphate precipitate was filtered out at 3.1 lbs/min and the filtrate was fed to a second phase separation tank where the fatty acid methyl esters and free fatty acids floated to the top and the glycerin and methanol sank to the bottom. The top, or light, phase was mixed with the light phase from the first phase separation tank and fed to the fatty acid methyl esters fractionation column. The pH of the heavy phase was adjusted back to 7.3 with 0.14 lbs/min potassium hydroxide and fed to the glycerin fractionation column.

The glycerin fractionation column recovered 10 lbs/min of methanol and 40 lbs/min of glycerin. The glycerin produced had a purity greater than 95 percent with non-detectable concentrations of salts and methanol. This glycerin stream was recycled back to the glycerin feed tank for the glycerolysis reaction and an additional 4 lbs/min of fresh glycerin was added to the glycerin feed tank to provide enough glycerin feed for the glycerolysis reaction.

The two light phase streams were fed to the fatty acid methyl ester fractionation column where 2.1 lbs/min of methanol was recovered and 91 lbs/min of fatty acid methyl esters meeting ASTM D 6751-02 (Standard Specification for Biodiesel Fuel (B100) Blend Stock for Distillate Fuels) were produced.

Example No. 5

Rendered brown grease with a free fatty acid concentration of 37 percent by weight and 5 percent MIU (moisture, impurities and unsaponifiables) was fed to the invention at 100 lbs/min. The grease was filtered and titrated continuously as it was fed to the glycerolysis reactors. Glycerin was added at a rate of 24 lbs/min. The temperature of the grease and glycerin mixture was raised to 210° C. as it was fed into the first of the glycerolysis continuous stirred tank reactors. In the reactor, the pressure was reduced to 2 psia and the temperature was maintained. The vessel was fitted with an agitator to keep the immiscible liquids in contact. Water vapor produced by the reaction was removed through vents in the reactor headspace. The residence time in each of the glycerolysis reactors was 3.0 hours. The conversion of fatty acids to glycerides in the first vessel was 90 percent. The fatty acid concentration leaving the second reactor was maintained at 0.5 percent by weight.

The product from the glycerolysis reactors was cooled to 50° C. and fed to the transesterification reactors where a solution of potassium hydroxide in methanol was added. The potassium hydroxide was added at a rate of 1.2 lbs/min and mixed with 21 lbs/min of methanol. The transesterification took place in two continuous stirred tank reactors in series, each with a two-hour residence time.

The transesterified product was then fed to a phase separation tank where the majority of the fatty acid methyl esters and 10 percent of the unreacted methanol floated to the top. The glycerin, the majority of the unreacted methanol, some fatty acid methyl esters, potassium hydroxide and soaps sank to the bottom.

The bottom, or heavy, phase was sent to an acidification reactor where the potassium hydroxide catalyst added in the transesterification was reacted with 2.13 lbs/min phosphoric acid. The soaps converted back to free fatty acids and the potassium hydroxide was neutralized. The product of this acidification was monobasic potassium phosphate, which is not soluble in this system.

The monobasic potassium phosphate precipitate was filtered out at 2.7 lbs/min and the filtrate was fed to a second phase separation tank where the fatty acid methyl esters and free fatty acids floated to the top and the glycerin and methanol sank to the bottom. The top, or light, phase was mixed with the light phase from the first phase separation tank and fed to the fatty acid methyl ester fractionation column. The pH of the heavy phase was adjusted to 7.5 with 0.12 lbs/min potassium hydroxide and fed to the glycerin fractionation column.

The glycerin fractionation column recovered 10 lbs/min of methanol and 25.2 lbs/min of glycerin. The glycerin produced had a purity greater than 95 percent with non-detectable concentrations of salts and methanol. This glycerin stream was split into two streams: 24 lbs/min was recycled back to the glycerin feed tank for the glycerolysis reaction, and 1.2 lbs/min was collected for market.

The two light phase streams were fed to the fatty acid methyl ester fractionation column where 2.0 lbs/min of methanol was recovered, and 89.8 lbs/min of fatty acid methyl esters meeting ASTM D 6751-02 (Standard Specification for Biodiesel Fuel (B100) Blend Stock for Distillate Fuels) were produced.

Example No. 6

A feedstock containing about 0.3 weight percent of free fatty acids and about 99.3 weight percent of glycerides (the remainder being water and insoluble and unsaponifiable solids), at a flow rate of about 40.9 pounds per hour, was heated to 50° C. and added to a solution of potassium hydroxide (1 percent of the feedstock flow on a weight basis) in methanol (stoichiometric ratio of 2:1 methanol:bound fatty acids in glycerides). The transesterification took place in a single continuous stirred tank reactor with a ten-hour residence time.

The transesterification effluent stream flow rate was approximately 50.3 pounds per hour and consisted of approximately 79 weight percent of fatty acid methyl esters, 8 weight percent glycerin, 9 weight percent methanol, 1.6 weight percent glycerides, with the remainder being water, insoluble and unsaponifiable solids, and soaps.

This stream was separated in a flow-through separator into a light phase stream and a heavy phase stream, the light phase stream having a flow of 41.5 pounds per hour and a composition of approximately 94.26 weight percent fatty acid methyl esters, 5.6 weight percent methanol, 0.09 weight percent glycerides and 0.05 weight percent free glycerin.

Free glycerin concentrations in this and the other samples in this example were determined using an enzyme assay solution provided by Sigma-Aldrich, Inc. of St. Louis, Mo. in a kit with product code BQP-02. With this kit, free glycerin was measured by coupled, enzymatic reactions that ultimately produce a quinoneimine dye that shows an absorbance maximum at 540 nm. The absorbance peak was measured using a Bausch & Lomb Spectronic 20 spectrophotometer.

The light phase stream was analyzed for glycerin and found to contain approximately 490 ppm glycerin by weight. The light phase stream was introduced into a reactive distillation column maintained at 260° C. at a pressure of 150 mmHg. The overhead vapor stream from the column was condensed, producing a liquid stream with a flow rate of about 2.1 pounds per hour, consisting primarily of methanol with a glycerin content of 135 ppm. The bottoms liquid stream, having a flow rate of approximately 39.3 pounds per hour, consisted of approximately 98.5 weight percent fatty acid methyl esters, 1.5 weight percent glycerides, and only 3 ppm glycerin. The reactive distillation referenced in this paragraph is schematically displayed as FIG. 6.

The gravimetric flow rates calculated using these analyses of free glycerin in the feed to the column versus in the overhead and bottoms streams indicated that about 98 percent of the glycerin was reacted into other moieties in the distillation column rather than simply flowing either to the overhead or bottoms streams.

This bottoms liquid stream was further refined to produce a biodiesel stream of fatty acid methyl esters meeting ASTM D 6751-06 S15 (Standard Specification for Biodiesel Fuel (B100) Blend Stock for Distillate Fuels).

From the foregoing, it will be observed that numerous variations and modifications may be effected without departing from the true spirit and scope of the novel concepts of the invention.

What is claimed is:

1. A process for the production of purified biodiesel from glycerides comprising:
    (A) reacting glycerides with at least one alcohol in a transesterification reaction to produce a fatty acid alkyl ester stream;
    (B) purifying the fatty acid alkyl ester stream by reactive distillation, wherein the reactive distillation involves separating fatty acid alkyl esters from glycerin and unreacted alcohol while simultaneously reacting glycerin with free fatty acid to produce glycerides; and
    (C) producing purified biodiesel therefrom.

2. The process of claim 1, wherein the glycerides of step (A) are produced by converting fatty acids in a feedstock.

3. The process of claim 2, wherein the glycerides are prepared by mixing the feedstock and glycerin at an elevated temperature in the absence of a catalyst.

4. The process of claim 1, wherein step (A) comprises reacting the glycerides with the at least one alcohol in the presence of an alkali catalyst to produce a fatty acid alkyl ester stream containing glycerin and fatty acid alkyl esters.

5. The process of claim 2, wherein the feedstock is conditioned to remove solids prior to converting the feedstock to glycerides.

6. The process of claim 1, wherein the product of step (A) is separated gravimetrically into a fatty acid ester rich stream and a glycerin rich stream and further introducing to the glycerin rich stream an organic acid and producing a purified glycerin rich stream therefrom.

7. The process of claim 6, wherein the organic acid is a weak organic acid selected from the group consisting of acetic acid, formic acid and propionic acid.

8. The process of claim 7, wherein the weak organic acid is acetic acid.

9. The process of claim 1, wherein the at least one alcohol is a $C_1$-$C_5$ alcohol.

10. The process of claim 9, wherein the $C_1$-$C_5$ alcohol is methanol.

11. A process for producing biodiesel from glycerides comprising:
    (A) reacting glycerides with at least one alcohol in a transesterification reaction to produce a transesterification effluent stream of fatty acid esters and glycerin;
    (B) separating the transesterification effluent stream into a fatty acid ester rich stream and a glycerin rich stream;
    (C) purifying the fatty acid alkyl ester stream by reactive distillation, wherein the reactive distillation involves separating fatty acid alkyl esters from glycerin and unreacted alcohol while simultaneously reacting glycerin with free fatty acid to produce glycerides;
    (D) introducing an organic acid to at least one of the:
        (i.) transesterification effluent stream, and
        (ii.) glycerin rich stream; and
    (E) recovering biodiesel therefrom.

12. The process of claim 11, wherein the process is continuous.

13. The process of claim 11, wherein the glycerides of step (A) are obtained by reacting a feedstock containing free fatty acids with glycerin.

14. The process of claim 11, wherein the glycerides in step (A) are reacted with the at least one alcohol in the presence of an alkali catalyst.

15. The process of claim 11, wherein the at least one alcohol is a $C_1$-$C_5$ alcohol.

16. The process of claim 15, wherein the $C_1$-$C_5$ alcohol is methanol.

17. The process of claim 14, wherein the alkali catalyst is selected from the group consisting of sodium hydroxide and potassium hydroxide.

18. A process for the production of purified biodiesel from glycerides comprising:
    (A) reacting glycerides with at least one alcohol in a transesterification reaction to produce a first fatty acid alkyl ester stream;
    (B) separating the first fatty acid alkyl ester effluent stream into a second fatty acid ester rich stream and a glycerin rich stream;
    (C) purifying the second fatty acid alkyl ester stream by reactive distillation, wherein the reactive distillation involves separating fatty acid alkyl esters from glycerin and unreacted alcohol in the second fatty acid alkyl ester stream while simultaneously reacting glycerin with free fatty acid to produce glycerides; and
    (D) producing purified biodiesel therefrom.

19. The process of claim 18 wherein the separation step (B) uses a difference in densities to separate the two streams.

* * * * *